United States Patent [19]

Ishikawa et al.

[11] Patent Number: 5,523,105
[45] Date of Patent: Jun. 4, 1996

[54] IMPROVED MINT COMPOSITION AND METHOD FOR PRODUCING THE SAME

[75] Inventors: Hisashi Ishikawa, Saitama; Yoshihisa Suzuki; Anri Sakai, both of Kanagawa; Shigeki Ishizuka, Saitama, all of Japan

[73] Assignees: Lotte Company Limited; Toyotama Perfumery Co., Ltd., both of Tokyo, Japan

[21] Appl. No.: 340,147

[22] Filed: Nov. 15, 1994

[30] Foreign Application Priority Data

Nov. 24, 1993 [JP] Japan ................................ 5-293114

[51] Int. Cl.$^6$ ....................................... A23L 1/22
[52] U.S. Cl. ................ 426/538; 426/3; 426/650; 426/655; 426/659; 426/660
[58] Field of Search .................... 426/538, 650, 426/655, 3, 534, 651, 658, 659, 660

[56] References Cited

FOREIGN PATENT DOCUMENTS

| | | |
|---|---|---|
| 63-129958 | 6/1988 | Japan . |
| 63-130523 | 6/1988 | Japan . |
| 3-259058 | 11/1991 | Japan . |

OTHER PUBLICATIONS

Aust.J.Chem., 15, (1962) pp. 322–327.
Aust.J.Chem., 15, (1962) pp. 389–390.
Israel Journal of Chemistry, vol. 16, 1977, pp. 28–31.
Journal of Natural Products, vol. 51, No. 1, pp. 22–29, 1988.
J. Agric. Food Chem., 1992, 40, 2328–2330.

*Primary Examiner*—Leslie Wong
*Attorney, Agent, or Firm*—Flynn, Thiel, Boutell & Tanis

[57] ABSTRACT

To provide a composition containing a mint flavor with an improved taste, polygodial or a polygodial-containing plant extract is added thereto. Enhancement of the coolness, suppression of the bitter/offensive taste and an improvement of the long-lasting properties are imparted to the taste of the mint flavor, thus enabling the effective application of the mint flavor to foods, drinks, cosmetics, toothpastes, drugs, etc.

9 Claims, No Drawings

IMPROVED MINT COMPOSITION AND METHOD FOR PRODUCING THE SAME

FIELD OF INDUSTRIAL APPLICATION

This invention relates to a flavor composition which is prepared by adding polygodial, or a polygodial-containing plant extract, to a mint flavor. By using this flavor composition, the odor, taste, preference and long-lasting properties of products containing a mint flavor (for example, foods, drinks, cosmetics, toothpastes or drugs) can be improved.

PRIOR ART

Mint flavors, which are prepared from essential oils obtained through steam distillation of raw materials such as peppermint, spearmint and Japanese peppermint, have been widely used in, for example, candies, chewing gums, confectionery, toothpastes, cosmetics and drugs, either alone or in the form of a blend. These essential oils, each of which has a taste with an aroma, a coolness and a refreshing feel, have been used as an important flavor. These mint flavors differ in taste characteristics from each other, depending on their habitats and variety. Therefore, a mint flavor suitable for the purpose is selected from among them and used. Further, the tastes of the mint flavors are improved by, for example, purification through distillation or aging prior to use.

Meanwhile, polygodial, which occurs in, for example, *Polygonum hydropiper* belonging to the family Polygonaceae, *Drimys lanceolata* and *Warburgia stublmannii* and has the following structural formula [1], has been known as a hot taste component, see Aust. J. Chem., 15, 322 (1962).

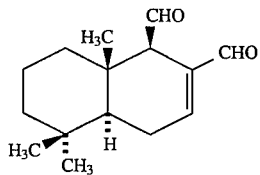

[1]

Owing to their hot tastes, these plants have been used as spices for a long time. See Aust. J. Chem., 15, 389 (1962). Also JP-A 3-259058 discloses the use of polygodial or an extract of *Polygonum hydropiper* containing polygodial as a preservative for miso (a fermented soybean paste).

Known physiological actions of polygodial include an antifeedant activity on insects, see Israel J. Chem., 16, 28 (1977), and an antimicrobial activity. See J. Natural Products, 51, 22 (1988). It has been also reported that polygodial exhibits a synergistic antimicrobial action on other antimicrobial agents. See J. Agric. Food Chem., 40, 2328 (1992).

As described above, mint flavors are essential components for products needing the refreshing coolness thereof. To make the taste characteristics thereof stable and long-lasting, attempts have been made to eliminate sulfur compounds and unsaturated terpene hydrocarbons contained in mint oils by distillation or to blend various mint oils with each other by taking their characteristics into consideration. However, neither the maintenance of the refreshing feel nor the elimination of the contaminating tastes can be fully achieved by these methods alone. Use of a large amount of a mint flavor is seemingly effective in the achievement of long-lasting taste characteristics. When used in a large amount, however, a mint flavor imparts a lasting bitterness to a product. Accordingly, it has been required to develop a mint flavor with little bitterness or a method for masking the bitterness.

DESCRIPTION OF THE INVENTION

In order to solve the above-mentioned problems, the present inventors have examined the effects of additives on mint oils. As a result, they have found out that polygodial and a polygodial-containing plant extract, from among a wide range of additives, are highly effective in the improvement of mint flavors, thus completing the present invention.

Accordingly, the present invention relates to a method for enhancing the coolness of a mint flavor, suppressing the bitter and offensive taste thereof and improving the long-lasting properties thereof which comprises adding polygodial or a polygodial-containing plant extract to the mint flavor which has been used as a flavoring agent and a composition therefor.

The invention provides, in other words, a method for improving the taste of a mint flavor, which comprises the step of adding, to the mint flavor, polygodial or a polygodial-containing plant extract in an effective amount for the taste-improvement of the mint flavor; a mint flavor composition comprising a mint flavor and polygodial and/or a polygodial-containing plant extract in an effective amount for taste improvement of the mint flavor; a taste-improver for a mint flavor, which comprises polygodial or a polygodial-containing plant extract; and a food composition comprising a foodstuff, a mint flavor and polygodial or a polygodial-containing plant extract.

It is preferable in the invention that the use is effected with 0.0001 to 1% by weight, based on the composition, of polygodial or 0.001 to 10% by weight, based on the composition, of a polygodial-containing plant extract; that the extract is obtained from *Polygonum hydropiper*, *Drimys lanceolata* or *Warburgia stublmannii*; that the extract is obtained by extracting polygodial from a polygodial-containing plant with an organic solvent and concentrating the extract; the composition comprises a mint flavor and a polygodial-containing plant extract in an effective amount for taste improvement of the mint flavor; or in the method, the coolness is strengthened or enhanced and the bitter and offensive taste is supressed.

The polygodial to be used in the present invention is contained in, for example, *Polygonum hydropiper* belonging to the family Polygonaceae, *Drimys lanceolata* and *Warburgia stublmannii*. A method for extracting and purifying polygodial from these plants is described in a report of Barnes et al. Aust. J. Chemistry, 15, 322 (1962). A polygodial-containing plant extract can be obtained by extracting a dry powder of such a plant as those cited above successively with petroleum ether and methanol. The obtained extract is further purified by liquid chromatography to thereby give polygodial in the crystalline form.

A polygodial-containing plant extract can be obtained from a dry plant by the above-mentioned method. The extractant to be used therefor is not restricted to petroleum ether but other organic solvents such as hexane, ethyl ether, acetone, ethanol and methanol are usable. This organic solvent extract is concentrated under a reduced pressure. Thus, a polygodial-containing plant extract can be obtained.

To prepare the mint flavor composition according to the present invention, either the polygodial or the polygodial-containing plant extract obtained by the above-mentioned method may be used. It is recommended that the content of polygodial ranges from 0.0001 to 1% by weight, preferably from 0.005 to 0.1% by weight, while the content of the polygodial-containing plant extract ranges from 0.001 to 10% by weight, preferably from 0.01 to 1% by weight, each based on the whole mint flavor composition.

EXAMPLES

To further illustrate the present invention in greater detail, and not by way of limitation, the following Examples will be given.

Preparation Example 1

To 500 g of a dry powder of Polygonum hydropiper was added 5 l of petroleum ether to effect extraction under stirring. The petroleum ether extract was concentrated under reduced pressure at a temperature of 35° C. or below and extracted again with 70% methanol repeatedly. To this methanol extract was added the same amount of a 10% aqueous solution of sodium chloride followed by extraction with ether. After concentrating the ether extract, the concentrate was dissolved in 100 ml of petroleum ether and applied to a silica gel column. This column was thoroughly washed with petroleum ether. Then a polygodial-containing fraction eluted with a mixture of petroleum ether with benzene (1:1) was concentrated. After adding petroleum ether thereto and recrystallizing, 230 mg of polygodial was obtained as a crystalline product.

By repeating the above-mentioned separation/purification process, 125 mg of polygodial was obtained from 320 g of a dry powder of Drimys lanceolata.

The melting point of the crystals thus obtained was from 56° to 57° C. while the elemental composition thereof was $C_{15}H_{22}O_2$, which agreed with the reported data. See Aust. J. Chem., 15, 322 (1962).

Preparation Example 2

500 g of a dry powder of Drimys lanceolata was twice extracted with 2 liters of hexane. The hexane extract was concentrated under reduced pressure at a temperature of 35° C. or below. Thus, 28 g of a dark brown, oily concentrate was obtained.

Preparation Example 3

By repeating the procedure of Preparation Example 2, 9.1 g of a dark brown, oily concentrate was obtained from 120 g of a dry powder of Polygonum hydropiper.

Examples 1 and 2

1) To 75 g of peppermint oil were added 15 g of L-menthol and 10 g of an edible fat to thereby prepare a mint flavor base (A).

2) To 100 g of the mint flavor base (A) was added 0.05 g of polygodial obtained in the above Preparation Example 1. After thorough mixing, a mint flavor composition (B) (Example 1) was obtained.

3) To 100 g of the mint flavor base (A) was added 0.6 g of the Drimys lanceolata extract obtained in the above Preparation Example 2. After thorough mixing, a mint flavor composition (C) (Example 2) was obtained.

Next, 0.8% by weight portions of the mint flavor base (A), the mint flavor composition (B) and the mint flavor composition (C) were each added to a gum-perfuming base and chewing gum bars were prepared experimentally. Then these chewing gum samples were organoleptically evaluated by 20 panelists.

As the results given in Tables 1 and 2 show, the chewing gum sample containing the mint flavor composition (B) and the one containing the mint flavor composition (C) each showed remarkable improvements in coolness, suppression of the bitter/offensive taste and long-lasting properties of the taste, compared with the control sample containing the mint flavor base (A).

TABLE 1

| Evaluation item | Ex. 1 Chewing gum containing mint flavor composition (B) | Control Chewing gum containing mint flavor base (A) |
|---|---|---|
| Strong coolness | 18 | 2 |
| Suppressed bitter/offensive taste | 15 | 5 |
| Long-lasting taste | 13 | 7 |

TABLE 2

| Evaluation item | Ex. 2 Chewing gum containing mint flavor composition (C) | Control Chewing gum containing mint flavor base (A) |
|---|---|---|
| Strong coolness | 19 | 1 |
| Suppressed bitter/offensive taste | 13 | 7 |
| Long-lasting taste | 15 | 5 |

Example 3

70 g of peppermint oil, 20 g of L-menthol, 5 g of winter green oil, 2 g of eucalyptus oil and 3 g of an edible fat were well mixed together to thereby give a mint flavor base (D). Then, 0.6 g of the Polygonum hydropiper extract obtained in the above Preparation Example 3 was added thereto. Thus, a mint flavor composition (E) (Example 3) was obtained.

Subsequently, 0.2% by weight portions of the mint flavor base (D) and the mint flavor composition (E) were added to candies which had been prepared from granulated sugar and starch syrup in a conventional manner to thereby experimentally prepare candy samples. Then these samples were organoleptically evaluated by 20 panelists.

As the results given in Table 3 show, the candy sample containing the mint flavor composition (E) showed remarkable improvements in coolness, suppression of bitter/offensive taste and long-lasting properties of taste, compared with the control sample containing the mint flavor base (D) alone, though the former sample showed a hotness.

TABLE 3

| Evaluation item | Ex. 3 Candy containing mint flavor composition (E) | Control Candy containing mint flavor base (D) |
|---|---|---|
| Strong coolness | 15 | 5 |
| Hotness | 16 | 4 |
| Suppressed | 14 | 6 |

TABLE 3-continued

| Evaluation item | Ex. 3 Candy containing mint flavor composition (E) | Control Candy containing mint flavor base (D) |
| --- | --- | --- |
| bitter/offensive taste | | |
| Long-lasting taste | 12 | 8 |

Example 4

6 g of peppermint oil, 0.5 g of L-menthol, 0.05 g of cinnamon oil, 0.75 g of clove oil, 0.002 g of fennel oil, 75 g of ethanol and 17.48 g of propylene glycol were well mixed together to thereby give a mint flavor base (F). Then 0.2 g of the *Drimys lanceolata* extract obtained in the above Preparation Example 2 was added thereto. Thus a mint flavor composition (G) (Example 4) was obtained.

Subsequently, 0.5% by weight portions of the mint flavor base (F) and the mint flavor composition (G) were added to an oral refresher prepared in accordance with Japanese Patent Laid-Open No. 58912/1985, followed by the organoleptic evaluation of the obtained samples by 20 panelists.

As the results given in Table 4 show, the oral refresher sample containing the mint flavor composition (G) showed remarkable improvements in coolness, suppression of bitter/offensive taste and long-lasting properties of taste, compared with the control sample containing the mint flavor base (F).

TABLE 4

| Evaluation item | Ex. 4 Oral refresher contianing mint flavor composition (G) | Control Oral refresher containing mint flavor base (F) |
| --- | --- | --- |
| Strong coolness | 17 | 3 |
| Suppressed bitter/offensive taste | 12 | 8 |
| Long-lasting taste | 13 | 7 |

What is claimed is:

1. A method for improving the taste of a mint flavored composition, which comprises the step of adding, to the mint flavored composition, polygodial or a polygodial-containing plant extract in an amount of 0.0001 to 1% by weight, based on the composition, of polygodial or 0.001 to 10% by weight, based on the composition, of a polygodial-containing plant extract to enhance the coolness and suppress the bitter and offensive taste of the mint flavor.

2. The method as claimed in claim 1, in which the polygodial-containing plant extract is added.

3. A mint flavored composition which comprises a mint flavor, 0.0001 to 1% by weight, based on the composition, of polygodial or 0.001 to 10% by weight, based on the composition, of a polygodial-containing plant extract.

4. The composition as claimed in claim 3, which comprises a mint flavor and 0.001 to 10% by weight of a polygodial-containing plant extract.

5. The composition as claimed in claim 4, in which the extract is obtained from *Polygonum hydorpiper, Drimys lanceolata* or *Warburgia stublmannii*.

6. The composition as claimed in claim 4, in which the extract is obtained by extracting polygodial from a polygodial-containing plant with an organic solvent and concentrating the extract.

7. The composition as claimed in claim 3, which comprises 0.005 to 0.1% by weight, based on the composition, of polygodial or 0.01 to 1% by weight, based on the composition, of a polygodial-containing plant extract.

8. A food composition comprising a foodstuff and the mint flavored composition of claim 3.

9. The composition as claimed in claim 8, wherein said foodstuff is selected from the group consisting of chewing gum, candy, and confectionery.

\* \* \* \* \*